United States Patent [19]
Smith et al.

[11] Patent Number: 5,972,203
[45] Date of Patent: Oct. 26, 1999

[54] HYDROCARBON CONVERSION CATALYST AND ITS USE

[75] Inventors: Robert Scott Smith, Houston; Gary D. Mohr, League City, both of Tex.

[73] Assignee: Exxon Chemical Patents Inc., Houston, Tex.

[21] Appl. No.: 08/865,635

[22] Filed: May 29, 1997

Related U.S. Application Data

[60] Provisional application No. 60/018,546, May 29, 1996.

[51] Int. Cl.[6] ........................................... C10G 11/05
[52] U.S. Cl. .......................... 208/113; 208/112; 208/120; 208/114; 208/135; 585/481; 585/467; 585/533; 585/275; 585/277; 585/428; 585/444; 585/721
[58] Field of Search ..................................... 208/114, 113, 208/135, 120; 585/481, 467

[56] References Cited

FOREIGN PATENT DOCUMENTS 0293926  12/1988  European Pat. Off. .
0293937  12/1988  European Pat. Off. .

*Primary Examiner*—Melane Myers
*Attorney, Agent, or Firm*—Edward F. Sherer

[57] ABSTRACT

There is provided catalysts and conversion processes for converting hydrocarbons using the catalysts. The catalysts comprises a first alumino-phosphospho-molecular sieves and a binder comprising a second alumino-phopho-molecular sieves. Exemplary conversion processes include the conversion of oxygenates to olefins, dewaxing, reforming, dealkylation, dehydrogenation, transalkylation, alkylation, and isomerization.

30 Claims, No Drawings

HYDROCARBON CONVERSION CATALYST AND ITS USE

This application claims benefit to U.S. provisional application Ser. No. 60/018,546 filed May 29, 1996.

FIELD OF INVENTION

This invention relates to crystalline alumino-phospho-molecular sieves that are bound by crystalline alumino-phospho-molecular sieves and their use in hydrocarbon conversion processes.

BACKGROUND OF THE INVENTION

Crystalline microporous molecular sieves, both natural and synthetic, have been demonstrated to have catalytic properties for various types of hydrocarbon conversion processes. In addition, the crystalline microporous molecular sieves have been used as adsorbents and catalyst carriers for various types of hydrocarbon conversion processes, and other applications. These molecular sieves are ordered, porous, crystalline material having a definite crystalline structure as determined by x-ray diffraction, within which there are a large number of smaller cavities which may be interconnected by a number of still smaller channels or pores. The dimensions channels of these pores are such as to allow adsorption of molecules with certain dimensions while rejecting those with larger dimensions. The interstitial spaces or channels formed by the crystalline network enable molecular sieves, to be used as molecular sieves in separation processes, catalysts and catalyst supports in a wide variety of hydrocarbon conversion processes.

One family of crystalline microporous molecular sieves is molecular sieves containing framework tetrahedral units of silica ($SiO_2$) and optionally alumina ($AlO_2$). Another family of crystalline microporous molecular sieves contain framework tetrahedral units of alumina ($AlO_2$) and phosphorous ($PO_2$). These molecular sieves are discussed in "Introduction To Zeolite Science and Practice", (H. van Bekkum, E. M. Flanigen, J. C. Jansen ed. 1991) which is hereby incorporated by reference. Examples of such ALPO-based molecular sieves ("ABMS") include SAPO, ALPO, MeAPO, MeAPSO, ELAPO, and ELAPSO. The composition of these molecular sieves is disclosed in Table I below:

TABLE I

Compositional Acronyms for $ALPO_4$-Based Materials

| Acronym | Framework T-Atoms | (Exemplary Me or El T-Atoms) |
|---|---|---|
| AlPO | Al, P | |
| SAPO | Si, Al, P | |
| MeAPO | Me, Al, P | (Co, Fe, Mg, Mn, Zn) |
| MeAPSO | Me, Al, P, Si | (Co, Fe, Mg, Mn, Zn) |
| ElAPO | El, Al, P | (As, B, Be, Ga, Ge, Li, Ti) |
| ElAPSO | El, Al, P, Si | (As, B, Be, Ga, Ge, Li, Ti) |

Within a pore of the crystalline molecular sieve, hydrocarbon conversion reactions such as paraffin isomerization, olefin skeletal or double bond isomerization, disproportionation, alkylation, and transalkylation of aromatics are governed by constraints imposed by the channel size of the molecular sieve. Reactant selectivity occurs when a fraction of the feedstock is too large to enter the pores to react; while product selectivity occurs when some of the products can not leave the channels or do not subsequently react. Product distributions can also be altered by transition state selectivity in which certain reactions can not occur because the reaction transition state is too large to form within the pores. Selectivity can also result from configuration constraints on diffusion where the dimensions of the molecule approach that of the pore system. Non-selective reactions on the surface of the molecular sieve, such reactions on the surface acid sites of the molecular sieve, are generally not desirable as such reactions are not subject to the shape selective constraints imposed on those reactions occurring within the channels of the molecular sieve.

ABMS have been used in the past as catalysts for hydrocarbon conversion. For instance, U.S. Pat. No. 4,741,820 involves the use in a reforming process using intermediate pore size molecular sieves such as SAPO which are bound by amorphorous material.

ABMS are usually prepared by crystallization of a supersaturated synthesis mixture. The resulting crystalline product is then dried and calcined to produce the molecular sieve powder. Although the powder has good adsorptive properties, its practical applications are severely limited because it is difficult to operate fixed beds with the powder. Therefore, prior to using the powder in commercial processes, the crystals are usually bound.

The powder is typically bound by forming aggregate of the molecular sieve such as a pill, sphere, or extrudate. The extrudate is usually formed by extruding the ABMS in the presence of an amorphorous binder and drying and calcining the resulting extrudate. The binder materials used are resistant to the temperatures and other conditions, e.g., mechanical attrition, which occur in various hydrocarbon conversion processes. Examples of binder materials include amorphous materials such as alumina, silica, titania, and various types of clays. It is generally necessary that the ABMS be resistant to mechanical attrition, that is, the formation of fines which are small particles, e.g., particles having a size of less than 20 microns.

Although such bound aggregates have much better mechanical strength than the powder, when such a bound material is used in a catalytic conversion process, the performance of the catalyst, e.g., activity, selectivity, activity maintenance, or combinations thereof, can be reduced because of the binder. For instance, since the binder is typically present in an amount of up to about 50 wt.% of crystals, the binder dilutes the adsorption properties of the material. In addition, since the bound molecular sieve is prepared by extruding or otherwise forming the molecular sieve with the binder and subsequently drying and calcining the extrudate, the amorphous binder can penetrate the pores of the molecular sieve or otherwise block access to the pores of the molecular sieve, or slow the rate of mass transfer to the pores of the molecular sieve which can reduce the effectiveness of the molecular sieve when used in hydrocarbon conversion processes and other applications. Furthermore, when the bound molecular sieve is used in catalytic conversion processes, the binder may affect the chemical reactions that are taking place within the molecular sieve and also may itself catalyze undesirable reactions which can result in the formation of undesirable products.

SUMMARY OF THE INVENTION

The present invention is directed to an ABMS bound ABMS catalyst which comprises first crystals of a first ABMS and a binder comprising second crystals of second ABMS and the use of the catalyst in hydrocarbon conversion processes. The structure type of the first ABMS can be the same as the second ABMS or can be different. The acidity of the second ABMS is preferably carefully controlled e.g., the acidity of the second ABMS can be the same as the first ABMS crystals or the acidity of the ABMS crystals can be higher or lower than the first ABMS crystals, so that the performance of the catalyst is further enhanced.

The catalyst of the present invention finds particular application in hydrocarbon conversion processes where catalyst acidity in combination with ABMS structure are important for reaction selectivity. Examples of such processes include catalytic cracking, alkylation, dealkylation, dehydrogenation, disproportionation, and transalkylation reactions. The catalyst of the present invention can also be used in other hydrocarbon conversion processes in which carbon containing compounds are changed to different carbon containing compounds. Examples of such processes include hydrocracking, isomerization, dewaxing, oxygenate conversion, oligomerization, and reforming processes.

DETAILED DESCRIPTION OF THE INVENTION

The catalyst of the present invention comprises first crystals of a first ABMS and a binder comprising second crystals of a second ABMS. Typical ABMS catalysts used in hydrocarbon conversion processes are normally bound with silica or alumina or other commonly used amorphous binders to enhance the mechanical strength of the ABMS.

Unlike typical crystalline molecular sieve catalysts used in hydrocarbon conversion processes which are normally bound with silica or alumina or other commonly used amorphous binders to enhance its mechanical strength, the catalyst of the present invention generally does not contain significant amounts of amorphous binders. Preferably, the catalysts contain less than 10 percent by weight, based on the weight of the first and second ABMS, of non-crystalline molecular sieve binder, more preferably contains less than 5 percent by weight, and, most preferably, the catalyst is substantially free of non-crystalline molecular sieve binder. Preferably, the second ABMS crystals bind the first ABMS crystals by adhering to the surface of the first ABMS crystals thereby forming a matrix or bridge structure which also holds the first crystals particles together. More preferably, the second ABMS particles bind the first ABMS by intergrowing so as to form a coating or partial coating on the larger first ABMS crystals and, most preferably, the second ABMS crystals bind the first ABMS crystals by intergrowing to form an attrition resistant over-growth over the first ABMS crystals.

Although the invention is not intended to be limited to any theory of operation, it is believed that one of the advantages of the ABMS bound ABMS catalyst of the present invention is obtained by the second ABMS crystals controlling the accessibility of the acid sites on the external surfaces of the first ABMS to reactants. Since the acid sites existing on the external surface of a ABMS catalyst are not shape selective, these acid sites can adversely affect reactants entering the pores of the ABMS and products exiting the pores of the ABMS. In line with this belief, since the acidity and structure type of the second ABMS can be carefully selected, the second ABMS does not significantly adversely affect the reactants exiting the pores of the first ABMS which can occur with conventionally bound ABMS catalysts and may beneficially affect the reactants exiting the pores of the first ABMS. Still further, since the second ABMS is not amorphous but, instead, is a molecular sieve, hydrocarbons may have increased access to the pores of the first ABMS during hydrocarbon conversion processes.

The terms "acidity", "lower acidity" and "higher acidity" as applied to crystalline molecular sieve are known to persons skilled in the art. The acidic properties of crystalline molecular sieves are well known. However, with respect to the present invention, a distinction must be made between acid strength and acid site density. Acid sites of a crystalline molecular sieves such as ABMS can be a Bronsted acid and/or a Lewis acid. The density of the acid sites and the number of acid sites are important in determining the acidity of the ABMS. Factors directly influencing the acid strength are (i) the chemical composition of the ABMS framework, i.e., relative concentration and type of tetrahedral atoms, (ii) the concentration of the extra-framework cations and the resulting extra-framework species, (iii) the local structure of the ABMS, e.g., the pore size and the location, within the crystal or at/near the surface of the ABMS, and (iv) the pretreatment conditions and presence of co-adsorbed molecules. As used herein, the terms "acidity", "lower acidity" and "higher acidity" refers to the concentration of acid sites irregardless of the strength of such acid sites which can be measured by ammonia absorption.

The term "average particle size" as used herein, means the arithmetic average of the diameter distribution of the crystals on a volume basis.

First and second ABMS suitable for used in the catalyst of the present invention include large pore ABMS, intermediate pore size ABMS, and small pore size ABMS. These crystalline molecular sieves are described in "Atlas of Zeolite Structure Types", eds. W. H. Meier and D. H. Olson, Buttersworth-Heineman, Third Edition, 1992, which is hereby incorporated by reference. Large pore ABMS generally have a pore size greater than about 7 Å and includes, for example, VFI, AET, AFI, AFO, ATS, FAU, structure type ABMS. Examples of large pore ABMS include ALPO-8, ALPO-41, SAPO-37, ALPO-37, ALPO-5, SAPO-5, ALPO-54, and MAPO-36. Medium pore size ABMS generally have a pore size from about 7 Å to about 5 Å to about 6.8 Å; and includes for example AEL, AFR, AFS, AFY, ATO, AFY, and APD structure type ABMS. Examples of medium pore ABMS include ELAPSO-11, ELAPSO-31, ELAPSO-40, ELAPSO-41, CoAPSO-11, CoAPSO-31, FeAPSO-11, FeAPSO-31, MgAPSO-11, MgAPSO-31, MnAPSO-11, MnAPSO-31, TiAPSO-11, ZnAPSO-11, ZnAPSO-31, CoMgAPSO-11, CoMnMgAPSO-11, MeAPO-11, TiAPO-11, TiAPO-31, ELAPO-11, ELAPO-31, ELAPO-40, ELAPO-41, SAPO-11, SAPO-31, SAPO-40, SAPO-41, ALPO-31, and ALPO-11. A small pore size ABMS has a pore size from about 3 Å to about 5.0 Å and includes, for example, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO. Examples of small pore ABMS include ALPO-17, ALPO-18, ALPO-52, ALPO-22, and ALPO-25.

The first ABMS will preferably have acidic activity and therefore will preferably be an ABMS that has an additional metal incorporated into the $AlPO_4$ lattice such as SAPO, MeAPSO, or ELAPSO. Examples of preferred first ABMS include SAPO-34, SAPO-11, GaSAPO-11, ZnSAPO-11, SAPO-17, NiSAPO-34, SAPO-5.

The structure type of the first ABMS will depend on the particular hydrocarbon process in which the catalyst is used. For example, when the catalyst is utilized for dewaxing, the first ABMS is preferably SAPO-11 or SAPO-40.

The average particle size of the first crystals is preferably from about 0.1 to about 15 microns. In many applications, the average particle size is preferably from about 1 to about 6 microns.

The structure type of the second ABMS can be the same or can be different from the first ABMS. Preferably, the second ABMS will have low acidity and more preferably will be substantially non-acidic. The preferred non-acidic ABMSs are aluminophosphates such as ALPO-17, ALPO-18, ALPO-11, ALPO-5, ALPO-41, GaALPO-11, ZnALPO-11. The pore size of the second ABMS will preferably be a pore size that does not significantly restrict access of the hydrocarbon feedstream to the pores of the first ABMS. For instance, when the materials of the feedstream which are to be converted have a size from 5 Å to 6.8 Å, the second ABMS will preferably be a large pore size ABMS or a intermediate pore size ABMS.

The second ABMS is preferably present in the catalyst in an amount in the range of from about 10 to about 60% by weight based on the weight of the first ABMS but the amount of second ABMS present will usually depend on the hydrocarbon process in which the catalyst is utilized. More preferably, the amount of second ABMS present in an amount of from about 20 to about 50% by weight.

The second ABMS crystals preferably have a smaller size than the first ABMS crystals. The second ABMS crystals preferably have an average particle size of less than 1 micron, preferably from about 0.1 to less than 0.5 micron. The second ABMS crystals, in addition to binding the first ABMS particles and maximizing the performance of the catalyst will preferably intergrow and to form an overgrowth which coats or partially coats the first ABMS. Preferably, the coating will be resistant to attrition.

The catalysts of the present invention are preferably prepared by a three step procedure. The first step involves the synthesis of the first ABMS. Processes for preparing the first ABMS are known in the art.

In the next step, a alumina-bound ABMS is prepared preferably by mixing a mixture comprising the ABMS crystals, alumina, water and optionally an extrusion aid until a homogeneous composition in the form of an extrudable paste develops. The alumina binder used in preparing the alumina bound ABMS aggregate is preferably a alumina sol. The amount of ABMS in the extrudate when dry will range from about 30 to 90% by weight, more preferably from about 40 to 90% by weight, with the balance being primarily alumina, e.g., about 10 to 60% by weight alumina.

The resulting paste is then molded, e.g. extruded, and cut into small strands, e.g., approximately 2 mm diameter extrudates, which are dried at 100–150° C. for a period of 4–12 hours. Preferably the dried extrudates are then calcined in air at a temperature of from about 400° C. to 550° C. for a period of from about 1 to 10 hours. This calcination step also destroys the extrusion aid if present.

Optionally, the alumina-bound aggregate can be made into a very small crystals which have application in fluid bed processes such as catalytic cracking. This preferably involves mixing the ABMS with a alumina containing matrix solution so that an aqueous solution of ABMS and alumina binder is formed which can be sprayed dried to result in small fluidizable alumina-bound aggregate crystals. Procedures for preparing such aggregate crystals are known to persons skilled in the art. An example of such a procedure is described by Scherzer (Octane-Enhancing Zeolitic FCC Catalysts, Julius Scherzer, Marcel Dekker, Inc. New York, 1990). The fluidizable alumina-bound aggregate crystals, like the alumina bound extrudates described above, would then undergo the final step described below to convert the alumina binder to a second ABMS.

The final step in the three step catalyst preparation process is the conversion of the alumina present in the alumina-bound catalyst to a second ABMS which serves to bind the residual the ABMS crystals together. To prepare the catalyst, the alumina-bound aggregate is preferably first aged in an appropriate aqueous solution at elevated temperature. Next, the contents of the solution and the temperature at which the aggregate is aged should be selected to convert the amorphous alumina binder into a second ABMS. The newly-formed ABMS is produced as crystals. The crystals may grow on and/or adhere to the initial ABMS crystals, and may also be produced in the form of new intergrown crystals, which are generally much smaller than the initial crystals, e.g., of sub-micron size. These newly formed crystals may grow together and interconnect thereby causing the larger crystals to become bound together.

The nature of the ABMS formed in the secondary synthesis conversion of the alumina to ABMS may vary as a function of the composition of the secondary synthesis solution and synthesis aging conditions. The secondary synthesis solution is an aqueous ionic solution containing a source of phosphoric acid and a templating agent sufficient to convert the alumina to the desired ABMS.

The catalyst of the present invention may be further ion exchanged as is known in the art either to replace at least in part the original alkali metal present in the first ABMS with a different cation, e.g., a Group 1B to VIII Periodic Table metal such as nickel, copper, zinc, palladium, platinum, calcium or rare earth metal, or to provide a more acidic form of the catalyst by exchange of alkali metal with intermediate ammonium, followed by calcination to remove ammonia and acidic hydrogen form. The acidic form may be readily prepared by ion exchange using a suitable acidic reagent such as ammonium nitrate. The catalyst may then be calcined at a temperature of 400–550° C. for a period of 10–45 hours to remove ammonium cations. Ion exchange is preferably conducted after formation of the catalysts. Particularly preferred cations are those which render the material catalytically active, especially for certain hydrocarbon conversion reactions. These include hydrogen, rare earth metals, and metals of Groups IIA, IIIA, IVA, VA, IB, IIB, IIIB, IVB, VB, VIB, VIIB, and VIII of the Periodic Table of the Elements. Examples of suitable metals include platinum, palladium, rhodium, iridium, iron, molydenium, cobalt, tungsten, nickel, manganese, titanium, zirconium, vanadium, hafnium, zinc, tin, lead, chromium, etc. The catalytically active metal is preferably present in an amount of from about 0.05 to about 3.0 weight percent based on the weight of first ABMS.

The catalyst of the present invention can be used in processing hydrocarbon feedstocks. Hydrocarbon feedstocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbon feed is to undergo, the feed can contain metal or can be free of metals. Also, the feed it can also have high or low nitrogen or sulfur impurities.

The conversion of hydrocarbon feeds can take place in any convenient mode, for example, in fluidized bed, moving bed, or fixed bed reactors depending on the types of process desired.

The catalysts of the present invention by itself or in combination with one or more catalytically active substances can be used for a variety of organic, e.g., hydrocarbon compound conversion processes. Examples of such hydrocarbon conversion processes include, as non-limiting examples, the following:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (volume of the catalyst, feed rate from about 10 milliseconds to about 10 seconds.

(B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100 $hr^{-1}$.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 1000 $hr^{-1}$ and an aromatic hydrocarbon/polyalkylaromatic hydrocarbon mole ratio of from about 1/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 100 $hr^{-1}$ and an aromatic hydrocarbon/alkylating agent mole ratio of from about 1/1 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1. The resulting product from the reaction are long chain alkyl aromatics which when subsequently sulfonated have particular application as synthetic detergents.

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$;

(I) The hydrocracking of heavy petroleum feedstocks, cyclic stocks, and other hydrocrack charge stocks. The catalyst will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Typical reaction conditions include temperatures from about 100° C. to about 250° C., a pressure of from about 100 to about 800 psig, a WHSV-olefin from about 0.4 $hr^{-1}$ to about 0.8 $hr^{-1}$, a WHSV-reformate of from about 1 $hr^{-1}$ to about 2 $hr^{-1}$ and, optionally, a gas recycle from about 1.5 to 2.5 vol/vol fuel gas feed.

(K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 100° C. to about 400° C. and pressures from about 50 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 $hr^{-1}$ to about 10 $hr^{-1}$.

(M) The conversion of light paraffins to olefins and/or aromatics such as is disclosed in U.S. Pat. No. 5,283,563, which is hereby incorporated by reference. Typical reaction conditions include temperatures from about 425° C. to about 760° C. and pressures from about 10 to about 2000 psig.

(N) The conversion of light olefins to gasoline, distillate and lube range hydrocarbons. Typical reaction conditions include temperatures of from about 175° C. to about 375° C. and a pressure of from about 100 to about 2000 psig.

(O) Two-stage hydrocracking for upgrading hydrocarbon streams having initial boiling points above about 200° C. to premium distillate and gasoline boiling range products or as feed to further fuels or chemicals processing steps in a first stage using in the first stage the catalyst comprising one or more catalytically active substances, e.g., a Group VIII metal, and the effluent from the first stage would be reacted in a second stage using a second catalyst comprising one or more catalytically active substances, e.g., a Group VIII metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10;

(P) A combination hydrocracking/dewaxing process in the presence of the catalyst comprising a hydrogenation component. Typical reaction conditions including temperatures from about 350° C. to about 400° C., pressures from about 1400 to about 1500 psig, LHSVs from about 0.4 to about 0.6 and a hydrogen circulation from about 3000 to about 5000 SCF/bbl.

(Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions including temperatures from about 20° C. to about 200° C., pressures from 2 to about 200 atm, WHSV (gram-olefin per hour gram-catalyst) from about 0.1 hr$^{-1}$ to about 200 hr$^{-1}$ and an alcohol to olefin molar feed ratio from about 0.1/1 to about 5/1.

(R) The disproportionation of toluene to make benzene and paraxylene. Typical reaction conditions including a temperature of from about 200° C. to about 760° C., a pressure of from about atmospheric to about 60 atmosphere (bar), and a WHSV of from about 0.1 hr$^{-1}$ to about 30 hr$^{-1}$.

(S) The conversion of naphtha (e.g. C6–C10) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the catalyst at a temperature in the range of from about 400° C. to 600° C., preferably 480° C. to 550° C. at pressures ranging from atmospheric to 40 bar, and liquid hourly space velocities (LHSV) ranging from 0.1to 15.

(T) The adsorption of alkyl aromatic compounds for the purpose of separating various isomers of the compounds.

(U) The conversion of oxygenates, e.g., alcohols, such as methanol, or ethers, such as dimethylether, or. mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100;

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with the catalyst at a temperature in the range of from about 250° C. to about 800°0 C., a LHSV of from about 0.2 to about 50 and a hydrocarbon partial pressure of from about 0.1 to about 50 atmospheres. Temperatures below about 250°0 C. may be used to oligomerize the feedstock when the feedstock is in the liquid phase when contacting the catalyst. Thus, when the olefin feedstock contacts the catalyst in the liquid phase, temperatures of from about 10° C. to about 250° C. may be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

(X) The isomerization of ethylbenzenes to xylenes. Exemplary conditions include a temperature from 600°–800° F., a pressure from 50 to 500 psig, and a LHSV of from about 1 to about 10.

In general, therefore, catalytic conversion conditions over a catalyst comprising the catalyst include a temperature of from about 100° C. to about 760° C., a pressure of from about 0.1 atmosphere (bar) to about 200 atmospheres (bar), a weight hourly space velocity of from about 0.08 hr$^{-1}$ to about 2,000 hr$^{-1}$.

Although many hydrocarbon conversion processes prefer that the second ABMS crystals have lower acidity to reduce undesirable reactions external to the first ABMS crystals, some processes prefer that the second ABMS crystals have higher acidity, e.g., the acidity be tailored so as to catalyze desirable reactions. Such processes are of two types. In the first type, the acidity and the structure type of the second ABMS is tailored to match the acidity and the crystallographic type of the first ABMS. By doing so, the catalytically active material per weight of formed catalyst will be increased thereby resulting in increased apparent catalyst activity. Such a catalyst would also be benefited by the greater adsorption, e.g., accessibility and reduced non-selective surface acidity.

The second type of process that can be benefited by tailoring the acidity of the second ABMS phase is one where two or more reactions are taking place within the ABMS catalyst. In such a process, the acidity and/or structure type of the second phase ABMS may be tailored so that it is different than that of the first ABMS, but does not have to be essentially void of acidic sites. Such a catalyst would be comprised of two different ABMS that could each be separately tailored to promote or inhibit different reactions. A process using such a catalyst would not only benefit from greater apparent catalyst activity, greater ABMS accessibility, and reduced non-selective surface acidity possible with the catalyst, it would also benefit from a tailored product.

Combined xylene isomerization/ethylbenzene dealkylation processes would benefit from this type of catalyst. An isomerization/ethylbenzene dealkylation catalyst could be tailored such that ethylbenzene dealkylation would primarily occur within the first ABMS crystals, and xylenes isomerization would primarily occur within the second ABMS crystals. By tailoring a catalyst in this way, a balance between the two reactions can be achieved that could not otherwise be achieved with a catalyst containing only one ABMS.

The catalysts of the present invention had particular application in the procedures set forth below.

A process where long straight chain hydrocarbons contained in a hydrocarbon stream of high pour point and high viscosity are isomerized to branched hydrocarbons via contact with an ALPO bound SAPO catalyst to give a hydrocarbon fluid with reduced pour point and lower viscosity. The SAPO component is an intermediate pore size molecular sieve and has an active metal for hydrogenation/dehydrogenation reactions and is acidic. The ALPO component can be either the same structural type or different and has little or no metal component and is non-acidic. The hydrocarbon is contacted with the catalyst at 150–650 ° C. in the presence of hydrogen gas at 15–3000 psig pressure with a WHSV of 0.1–20 hr$^{-1}$.

A process where $C_2$–$C_5$ paraffins and olefins are converted to mono-nuclear aromatic compounds by contacting the paraffins with an ALPO bound SAPO catalyst at 400–700° C. at a pressure of 1–100 atmospheres and WTHSV of 0.1–200 hr$^{-1}$. The SAPO component is a medium pore molecular sieve and may or may not contain a metal oxide component such as ZnO or $Ga_2O_3$. The ALPO material may or may not be the same structural type and may contain metal oxide components such as ZnO or $Ga_2O_3$.

A process to convert methanol to light olefins where the methanol is contacted with the ALPO bound SAPO at 400–600° C. at pressure of 1–100 atmospheres sometimes in the presence of a diluent such as steam with a WHSV or 0.1–100 hr$^{-1}$. At least one of the ALPO or SAPO components should have an 8-ring pore opening such as SAPO-34, SAPO-17, or ALPO-17. The other component could be also have an 8-ring pore opening or could be either 10 or 12 ring openings. Possible non-limiting combinations are ALPO-17 bound SAPO-11 or ALPO-17 bound SAPO-34.

The catalysts of the present invention find particular application in reactions involving aromatization and/or dehydrogenation. They are particularly useful in a process for the dehydrocyclization and/or isomerization of acyclic hydrocarbons in which the hydrocarbons are contacted at a temperature of from 370° C. to 600° C., preferably from 430° C. to 550° C. with the catalysts, preferably having at least 90% of the exchangeable cations as alkali metal ions and incorporating at least one Group VIII metal having dehydrogenating activity, so as to convert at least part of the acyclic hydrocarbons into aromatic hydrocarbons.

The aliphatic hydrocarbons may be straight or branched chain acyclic hydrocarbons, and particularly paraffins such as hexane, although mixtures of hydrocarbons may also be used such as paraffin fractions containing a range of alkanes possibly with minor amounts of other hydrocarbons. Cycloaliphatic hydrocarbon such as methylcyclopentane may also be used. In a preferred aspect the feed to a process for preparing aromatic hydrocarbons and particularly benzene comprises hexanes. The temperature of the catalytic reaction may be from 370° C. to 600° C., preferably 430° C. to 550° C. and preferably pressures in excess of atmospheric are used, for example up to 2000 KPa, more preferably 500 to 1000 KPa. Hydrogen is usually employed in the formation of aromatic hydrocarbons preferably with a hydrogen to feed ratio of less than 10.

The following examples illustrate the invention:

EXAMPLE 1

I. Catalyst A—ALPO-5 bound SAPO-34

SAPO-34 bound by 30% by weight alumina was formed into AlPO-5 bound SAPO-34 as follows:

Amounts of 4.18 grams of 85% aqueous $H_3PO_4$, 10.78 grams of water, and 2.65 grams of tripropylamine (TPA) were added to a 300 ml Teflon lined autoclave in the order listed. The mixture was stirred to give a homogeneous solution. Next, 10 grams of dried extrudates (1/16" diameter) of the alumina bound SAPO-34 were added to the contents in the autoclave. The extrudates were completely covered by the liquid. The molar composition of the synthesis mixture was:

$TPA/Al_2O_3/P_2O_5/H_2O$ of 0.63/1.0/0.62/23.4

In the mixture, the alumina accounts for only the alumina binder of the extrudate and the $P_2O_5$ accounts for only 85% aqueous $H_3PO_4$. The autoclave was sealed and the mixture was heated in 2 hours to 200° C. and held without stirring for 24 hours at 200° C. The autoclave was cooled to room temperature and the mother liquor was decanted. The extrudates were washed with de-ionized water until the conductivity of the filtrate was less than 100 micro-Siemens. XRD analysis showed typical patterns for both SAPO-34 and ALPO-5.

II. Catalyst B—ALPO-11 bound SAPO-34

SAPO-34 bound by 25% by weight alumina was formed into ALPO-11 bound SAPO-34 as follows:

Amounts of 6.36 grams of 85% aqueous $H_3PO_4$, 18.02 grams of water, and 2.82 grams of dipropylamine (DPA) were added to a 100 ml teflon lined autoclave in the order listed. The mixture was stirred to give a homogeneous solution. Next, 15.00 grams of dried extrudates (1/16" diameter) of the alumina bound SAPO-34 were added to the contents in the autoclave. The extrudates were completely covered by the liquid. The molar composition of the synthesis mixture was:

$DPA/Al_2O_3/P_2O_5/H_2O$ of 0.76/0.75/1.0/30.9

In the mixture, the $Al_2O_3$ accounts for only the alumina binder of the extrudate and the $P_2O_5$ accounts for only the 85% aqueous $H_3PO_4$. The autoclave was sealed and heated in 2 hours to 200° C. and held without stirring for 22 hours at 200° C. The autoclave was cooled to room temperature and the mother liquor was decanted. The extrudates were washed with de-ionized water until the conductivity of the filtrate was less than 100 micro-Siemens. XRD analysis showed typical patterns for both SAPO-34 and ALPO-11.

III. Catalyst C—ALPO-17 bound SAPO-34

SAPO-34 bound by 25% by weight alumina was formed into AlPO-5 bound SAPO-34 as follows:

Amounts of 6.35 grams of 25% aqueous $H_3PO_4$, 17.60 grams of water, and 2.77 grams of cyclohexalamine were added to a 300 ml Teflon lined autoclave in the order listed. The mixture was stirred to give a homogeneous solution. Next, 15.02 grams of dried extrudates (1/16" diameter) of the alumina bound SAPO-34 were added to the contents in the autoclave. The extrudates were completely covered by the liquid. The molar composition of the synthesis mixture was:

$1.00R_2O_5/1.01R/1.00Al_2O_3/39H_2O$

In the mixture, the alumina accounts for only the alumina binder of the extrudate and the $P_2O_5$ accounts for only 25% aqueous $H_3PO_4$. The autoclave was sealed and the mixture was heated in 2 hours to 200° C. and held for 48 hours at 200° C. The autoclave was cooled to room temperature, a small sample of extrudate removed, and then the mixture was heated to 200° C. in 2 hours and held at 200 C. for another 48 hours. The extrudates were allowed to cool and were washed 4 times with 800 ml of water. The conductivity of the last wash water was less than 26 $\mu$S/cm. The extrudates were then dried at 120° C. The amount of extrudates recovered was 17.3 grams. XRD analysis showed typical patterns for both SAPO-34 and ALPO-5.

EXAMPLE 2

Catalyst A, Catalyst B, and Catalyst C were tested for use in the conversion of oxygenates to olefins. The tests were carried out using the following procedure: 5.0 cc (approximately 2.7 grams) of each catalyst was mixed with 15 cc quartz beads and loaded into a 3/4" outer diameter 316 stainless steel tubular reactor which was heated by three-zone electric furnaces. The first zone acted as the preheating zone, vaporized the feed. The temperature of the center zone of the furnace was adjusted to 450° C. and the pressure was maintained at 1 atm. The reactor was purged first with nitrogen at 50 cc/min flow rate for 30 minutes. The feed had a 4:1 molar ratio of water to methanol and was pumped into the reactor at a rate calibrated to give a flow rate of about 0.7 $hr^{-1}$ WHSV. The effluent was analyzed at pre-determined intervals by an on-line gas chromatography fitted with both a thermal conductivity detector and a flame ionization detector. The results of these tests are shown below in Table II:

TABLE II

| Olefins Yield Conversion (wt. %) | Catalyst A | Catalyst B | Catalyst C |
| --- | --- | --- | --- |
| Methane | 5.7 | 1.6 | 1.5 |
| Ethylene | 24 | 45 | 47 |
| Propylene | 41 | 38 | 37 |
| $C_4$ | 27 | 15 | 14 |

The data shows that the catalysts have good ethylene and propylene selectivity and by tailoring the catalyst, product distribution can be varied.

What is claimed is:

1. A process for converting hydrocarbons comprising contacting a hydrocarbon feedstream under hydrocarbon conversion conditions with an ABMS catalyst bound by an ABMS which does not contain significant amounts of amorphorous binder and comprises:
   (a) first crystals of a first ABMS, and
   (b) a binder comprising second crystals of a second ABMS, said second crystals binding together said first crystals.

2. The process recited in claim 1, wherein said first crystals of said first ABMS have an average particle size greater than about 0.1 micron.

3. The process recited in claim 2, wherein said second crystals of said second ABMS have an average particle size that is less than said first crystals of said first ABMS.

4. The process recited in claim 3, wherein said second crystals are intergrown and form at least a partial coating on said first crystals.

5. The process recited in claim 3, wherein said first ABMS is a structure type selected from the group consisting of VFI, AET, AFI, AFO, ATS, FAU, AEL, AFR, AFS, AFY, ATO, AFY, APD, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO.

6. The process recited in claim 5, wherein said second ABMS is a structure type selected from the group consisting of VFI, AET, AFI, AFO, ATS, AFO, FAU, AEL, AFR, AFS, AFY, ATO, AFY, APD, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO.

7. The process recited in claim 6, wherein said second ABMS has lower acidity than the first ABMS.

8. The process recited in claim 6, wherein said second ABMS has higher acidity than the first ABMS.

9. The process recited in claim 6, wherein the hydrocarbon conversion is selected from the group consisting of cracking of hydrocarbons, dealkylation of aromatics, isomerization of alkyl aromatics, disproportionation of toluene, dehydrogenation of hydrocarbons, transalkylation of aromatics, alkylation of aromatics, reforming of naphtha to aromatics, conversion of paraffins and/or olefins to aromatics, conversion of oxygenates to hydrocarbon products, cracking of naphtha to light olefins, and dewaxing of hydrocarbons.

10. The process recited in claim 9, wherein said second ABMS has lower acidity than said first ABMS.

11. The process recited in claim 9, wherein the pore size of said first ABMS is larger than the pore size of said second ABMS.

12. The process recited in claim 9, wherein the pore size of said first ABMS is smaller than the pore size of said second ABMS.

13. The process recited in claim 9, wherein said first ABMS and second ABMS are intermediate pore size or small pore size ABMS.

14. The catalyst recited in claim 9, wherein said first ABMS and said second ABMS have different structure types.

15. The process recited in claim 9, wherein said first ABMS and said second ABMS have different structure types.

16. The process recited in claim 6, wherein said first ABMS and said second ABMS are independently selected from the group consisting of ALPO-8, ALPO-41, SAPO-37, ALPO-37, SAPO-31, SAPO-40, SAPO-41, ALPO-5, SAPO-5, ALPO-54, MAPO-36, SAPO-40, SAPO-11, ALPO-31, ALPO-11, ALPO-17, ALPO-18, ALPO-52, ALPO-22, and ALPO-25.

17. The process recited in claim 6, wherein said first ABMS is SAPO-37, SAPO-40, SAPO-5, MAPO-36, and SAPO-11.

18. The process recited in claim 17, wherein said first ABMS is SAPO.

19. The process recited in claim 18, wherein said second ABMS is ALPO.

20. The process recited in claim 6, wherein said first ABMS is SAPO-34, SAPO-11, GaSAPO-11, ZnSAPO-11, SAPO-17, NiSAPO-34, or SAPO-5.

21. The process recited in claim 6, wherein said second ABMS is ALPO-17, ALPO-18, ALPO-11, ALPO-5, ALPO-41, GaALPO-11, or ZnALPO-11.

22. The catalyst recited in claim 6, wherein said first crystals have an average particle size of from about 1 to 6 microns.

23. The catalyst recited in claim 22, wherein said second crystals have an average particle size of from about 0.1 to about 0.5 microns.

24. The process recited in claim 6, wherein said first crystals have an average particle size of from about 1 to 6 microns.

25. The process recited in claim 24, wherein said second crystals have an average particle size of from about 0.1 to about 0.5 microns.

26. The process recited in claim 3, wherein said hydrocarbon conversion is dehydrogenation.

27. The process recited in claim 3, wherein said hydrocarbon conversion is cracking.

28. The process recited in claim 3, wherein said hydrocarbon conversion is dewaxing.

29. The process recited in claim 3, wherein said hydrocarbon conversion is the conversion of oxygenates to olefins.

30. The process recited in claim 3, wherein said hydrocarbon conversion is reforming.

* * * * *